US009938318B2

(12) United States Patent
Schulz et al.

(10) Patent No.: US 9,938,318 B2
(45) Date of Patent: Apr. 10, 2018

(54) PROCESS FOR PRODUCTION OF FIBRINOGEN

(71) Applicant: OCTAPHARMA AG, Lachen (CH)

(72) Inventors: Petra Schulz, Vienna (AT); Rainer Pape, Vienna (AT); Werner Gehringer, Vienna (AT)

(73) Assignee: OCTAPHARMA AG, Lachen (CH)

( * ) Notice: Subject to any disclaimer, the term of this patent is extended or adjusted under 35 U.S.C. 154(b) by 0 days.

(21) Appl. No.: 15/164,736

(22) Filed: May 25, 2016

(65) Prior Publication Data

US 2016/0264619 A1 Sep. 15, 2016

Related U.S. Application Data

(62) Division of application No. 13/825,317, filed as application No. PCT/EP2011/066293 on Sep. 20, 2011, now Pat. No. 9,371,355.

(60) Provisional application No. 61/344,719, filed on Sep. 21, 2010.

(30) Foreign Application Priority Data

Sep. 20, 2010 (EP) .................................... 10177640

(51) Int. Cl.
*C07K 14/75* (2006.01)
*C07K 1/18* (2006.01)
*C07K 1/36* (2006.01)

(52) U.S. Cl.
CPC ................ *C07K 1/18* (2013.01); *C07K 1/36* (2013.01); *C07K 14/75* (2013.01)

(58) Field of Classification Search
CPC .................................................... C07K 14/75
See application file for complete search history.

(56) References Cited

U.S. PATENT DOCUMENTS

| 5,290,918 | A | * | 3/1994 | Bui-Khac | C07K 14/745 |
| | | | | | 530/381 |
| 5,834,420 | A | | 11/1998 | Laub et al. | |
| 6,037,457 | A | | 3/2000 | Lord | |
| 6,468,733 | B2 | | 10/2002 | Nur et al. | |
| 6,579,537 | B2 | * | 6/2003 | Seelich | A61L 24/106 |
| | | | | | 424/530 |
| 7,919,592 | B2 | | 4/2011 | Lengsfeld et al. | |
| 9,371,355 | B2 | * | 6/2016 | Schulz | C07K 14/75 |
| 2006/0009376 | A1 | | 1/2006 | Eibl | |
| 2008/0003272 | A1 | | 1/2008 | Rapp et al. | |
| 2008/0181878 | A1 | | 7/2008 | Farrell | |
| 2008/0207878 | A1 | | 8/2008 | Michel et al. | |
| 2011/0114524 | A1 | | 5/2011 | Eibl | |

FOREIGN PATENT DOCUMENTS

| CN | 1425024 A | 6/2003 |
| CN | 101703763 A | 5/2010 |
| EP | 0 131 740 A2 | 1/1985 |
| EP | 0 555 135 A1 | 8/1993 |
| EP | 0 771 324 A1 | 5/1997 |
| EP | 1 240 200 A1 | 9/2002 |
| EP | 1519944 A1 | 4/2005 |
| EP | 1457497 B1 | 10/2008 |
| EP | 1519944 B1 | 11/2009 |
| WO | WO-95/022316 A1 | 8/1995 |
| WO | WO-96/02571 A1 | 2/1996 |
| WO | WO-01/48016 A1 | 7/2001 |
| WO | WO-2009/155626 A2 | 12/2009 |
| WO | WO-2012038410 A1 | 3/2012 |
| WO | WO-2013135684 A1 | 9/2013 |

OTHER PUBLICATIONS

International Search Report and Written Opinion issued in PCT International Application No. PCT/EP2011/066293, dated Dec. 23, 2011.
International Preliminary Report on Patentability issued in PCT International Application No. PCT/EP2011/066293, dated Mar. 26, 2013.
International Search Report issued in International Application No. PCT/EP2013/054983, dated May 23, 2013.
International Preliminary Report on Patentability issued in PCT Application No. PCT/EP2013/054983, dated Sep. 16, 2014.
Goheen S. C. et al: "High-performance ion-exchange chromatography and adsorption of plasma proteins", Journal of Chromatography, Elsevier Science Publishers B.V., NL, vol. 816, No. 1, Aug. 7, 1998, pp. 89-96.
Chinese Office Action (with English translation) dated May 6, 2014, issued in Chinese Application No. 201180045268.1.
Pohl et al., "Effects of the deletion of the *Escherichia coil* frataxin homologue CyaY on the respirator NADH:ubiquinone oxidoreductase" BMC Biochemistry 2007, 8:13 1-10.
Tosoh Bioscience "Toyopearl GigaCap Q-650M for high capacity Anion Exchange Chromatography of small and large proteins," 2008.
GE Health Care "Ion Exchange Chromatography & Chromatofocusing Principles and Methods" 2010.
Sigma Aldrich "Analytical Enzymes Fibrinogen and Fibrin" 2004.
Third party submission under 37 CFR 1.290 filed on Aug. 7, 2015 for U.S. Appl. No. 14/382,712 published on Feb. 12, 2015 (14 pages).

\* cited by examiner

*Primary Examiner* — Karen Cochrane Carlson
(74) *Attorney, Agent, or Firm* — Keith G. Haddaway; Kerri M. Patterson

(57) ABSTRACT

The present invention relates to a method or process for the manufacture of a virus and prion save native fibrinogen concentrate of high purity and low amounts of fibrinopeptide A and fibronectin.

11 Claims, No Drawings

PROCESS FOR PRODUCTION OF FIBRINOGEN

CROSS-REFERENCES TO RELATED APPLICATIONS

This application is a divisional of U.S. patent application Ser. No. 13/825,317, filed Mar. 20, 2013 and published Oct. 17, 2013 as US 2013/0274444; which is a U.S. National Stage of International Application No. PCT/EP2011/066293, filed Sep. 20, 2011 and published Mar. 29, 2012 as WO2012/038410; which claims the benefit of U.S. Provisional Patent Application No. 61/344,719, filed Sep. 21, 2010; and which claims the benefit of European Patent Application No. 10177640.9, filed Sep. 20, 2010, all of which are hereby incorporated by reference in their entirety.

BACKGROUND OF THE INVENTION

Fibrinogen, also known as clotting factor I, plays a key role in haemostasis and wound healing. It is a glycoprotein synthesized in the liver with an apparent molecular weight of 340.000 Da, is composed of two dimers, each of them built of three pairs of non-identical polypeptide chains called Aα, Bβ and γ linked by disulfide bridges. It circulates in the blood stream at a concentration of approximately 150-400 µg/ml. Upon injury of blood vessels, blood platelets are activated and a plug is formed. Fibrinogen is involved in primary haemostasis by aiding cross-linking of activated platelets.

In parallel activation of the clotting cascade is initiated. As the endpoint, fibrinogen is converted into fibrin by proteolytic release of fibrinopeptide A and—at a slower rate—fibrinopeptide B by thrombin. The soluble fibrin monomers are assembled to double stranded twisted fibrils. Subsequently these fibrils are arranged in a lateral manner, resulting in thicker fibers. These fibers are then cross-linked by FXIIIa to a fibrin network, which stabilizes the platelet plug by interactions of the fibrin with activated platelets, resulting in a stable clot.

Disorders and Deficiencies

Congenital afibrinogenaemia is a rare bleeding disorder, where patients are suffering from inadequate clotting of the blood due to lacking or malfunction of fibrinogen. This medical condition might lead to spontaneous bleeding episodes or excessive bleeding after minor traumata or during interventional procedures.

Acquired deficiencies in fibrinogen are much more common than congenital afibrinogenaemia and may be induced by haemodilution or other events such as blood losses during surgery, traumata, disseminated intravascular coagulation (DIC) or sepsis.

Fibrinogen deficiencies can be corrected to normal fibrinogen levels in plasma of about 1.5-3 g/l by replacement therapy with intravenous infusion of fresh frozen plasma or cryoprecipitate. However, these treatments are afflicted with the risk of introduction of pathogens, e.g. viruses or prions, into a patient and are thereby generating additional disorders. It is thus advisable to intravenously apply virus inactivated fibrinogen compositions to restore fibrinogen at physiological levels in a save way.

While there exists fibrinogen in preparations called fibrin glue, fibrinogen adhesive, tissue glue and similar, these preparations are intended for topical use as powders, pastes, foams or in combination with fabrics as plaster on wounds, they are not useable for intravenous application as their consistency and composition would immediately initiate thrombotic events when being injected. These preparations additionally contain thrombin, calcium salts and relatively high amounts of coagulation factor XIII. Examples for such preparations are US-A1-2008/003272, WO-A-95/22316 or US-A1-2008/181878.

Processes for fibrinogen production are known from EP-B1-1 240 200 which relates to a method of purifying fibrinogen from a fibrinogen containing solution, comprising, application of a fibrinogen containing solution to an ion exchange matrix, under conditions such that fibrinogen binds to the matrix, washing the ion exchange matrix with a buffer solution comprising at least one ω-amino acid, eluting the fibrinogen from the matrix with a buffer consisting of 10 mM Tris, 10 mM citrate, 45 mM sucrose; and NaCl at a concentration of 200 mM to 1.0M, and optionally recovering the fibrinogen from the eluate.

EP-B1-0 771 324 refers to a process for production of a virus free fibrinogen concentrate is obtained by subjecting a solubilised plasma fraction containing fibrinogen to a chemical viral inactivation treatment, i.e. a S/D or solvent/detergent treatment, subjecting the resulting viral-inactivated fraction to precipitation in a solution containing an amino acid at an acidic pH to obtain a supernatant, filtering the supernatant to obtain a purified fibrinogen concentrate, and recovering the purified fibrinogen concentrate. The recovered fibrinogen concentrate is subjected ultra violet radiation for a second virus inactivation. The product is stabilized and lyophilized prior to a third virus inactivation.

EP-B1-1 519 944 teaches the use of an immobilized metal ion affinity chromatography matrix under conditions that the fibrinogen and plasminogen bind to the matrix, and selectively eluting the fibrinogen and 93% of plasminogen separately from the matrix.

EP-B1-0 555 135 discloses a method for production of an intravenously applicable fibrinogen by purification of a fibrinogen solution over an anion exchange gel based on cross-linked agarose comprising quaternary amine groups. The fibrinogen produced is said to be free of factor VIIIc.

EP-B1-1 457 497 refers to a process for removing viruses in fibrinogen solutions characterized by stabilization and freezing of the solution and subsequent thawing thereof. Separation of undissolved materials occurs prior to dilution of the protein and is followed by nanofiltration of the resultant solution using filters of a pore size smaller than 35 nm.

US-A1-2006/0009376 also discloses a method to manufacture fibrinogen. Following repeated dissolution and precipitation of fibrinogen to remove factor XIII.

Goheen, S. C. et al. report in Journal of Chromatography A. 816 (1998) 89-96, about HPLC ion-exchange chromatography of the plasma proteins albumin, fibrinogen, and immunoglobulin (G) on nonporous column materials containing either quarternary amine or sulfopropyl functional groups.

BRIEF SUMMARY OF THE INVENTION

One object of the invention is providing of a fibrinogen concentrate manufactured with dedicated pathogen eliminating and/or inactivation steps in the production process in order to overcome adverse reactions or development of pathogen related illnesses. Said pathogens are selected from the groups of bacteria, viruses and prions, such as prion protein scrapie ($PrP^{sc}$). Systemic application of such a fibrinogen product via intravenous route allows treatment of congenital afibrinogenaemia and acquired fibrinogen deficiencies. Application of this standardized fibrinogen concentrate allows fast treatment in emergency situations without time-consuming thawing of fresh frozen plasma and lowered volume load and reliable coagulation properties due to essentially constant composition.

A further object of this application is providing of a process to manufacture a concentrate on an industrial level, i.e. several hundreds to thousands of liters starting material, such as blood or blood plasma, although a small scale production, i.e. some 1/10 liter to some liters, is also possible.

These and further objects are accomplished by the process of the invention as claimed.

In general, the process of the invention for purification or manufacturing of fibrinogen from fibrinogen containing sources comprises the steps of:
  forming a fibrinogen enriched precipitate by adding at least one precipitating agent to the fibrinogen containing source;
  optionally isolating the fibrinogen enriched precipitate e.g. by centrifugation of said precipitate;
  taking up the fibrinogen enriched precipitate in an aqueous medium forming a fibrinogen containing solution, optionally followed by filtration and/or ultra/diafiltration;
  subjecting the fibrinogen containing solution to a chromatography on a stationary phase having strong anion exchanger groups by contacting said solution with said phase under conditions that fibrinogen binds to said phase;
  followed by an elution of fibrinogen from the stationary phase by means of an aqueous solution having a higher ionic strength than the ionic strength of the foregoing step, yielding a fibrinogen enriched fraction which is collected;
  optionally followed by subsequent steps of dilution and/or concentration of the fibrinogen enriched fraction;
  and optionally filling of the fibrinogen enriched fraction into suitable vials.

In one embodiment of the manufacturing process of the invention the fibrinogen containing source is selected from the group consisting of, blood plasma, plasma fractions, such as fraction I, or cryoprecipitate, cell cultures producing fibrinogen and/or supernatants of said cell cultures. If cryoprecipitate is not used as starting material, a fibrinogen containing intermediate as starting material is produced by well known methods like disclosed by Cohn, Kistler-Nitschmann and modifications thereof.

For obtaining a pharmaceutical usable product it is advantageous that the fibrinogen containing source is subjected to a virus inactivating process for example a solvent detergent process.

According to another embodiment of the invention the virus inactivation is performed prior to forming a fibrinogen enriched precipitate. However, it is also possible to perform a virus inactivation at a different stage.

According to yet another embodiment of the invention the removal of virus inactivating substances is performed by oil extraction and/or chromatography with strong anion exchangers.

A typical precipitating agent for use in the manufacturing process of the invention is selected from the group consisting of amino acids such as glycine, high salt concentrations (salting-out) or polyethylene glycol.

According to still another embodiment of the invention the taking up is resuspending of a paste in a buffer having a pH of 7.5 to 8.5.

According to a further embodiment of the invention the stationary phase has tertiary or quaternary amino groups.

The chromatography steps in the manufacturing process of the invention can in particular be performed in a column.

Typically the storage form of the filled fibrinogen enriched fraction is in liquid state, frozen state, preferably at <−15° C., most preferably below −30° C., or as lyophilisate.

Subject matter of the present invention is also a fibrinogen enriched fraction obtainable according to the manufacturing process of the invention. The fibrinogen enriched fraction of the invention contains e.g. 0.01-9.0 ng fibrinopeptide A per mg fibrinogen. Further the fibrinogen enriched fraction of the invention contains 0.80-1.10 mg fibrinogen-antigen per mg fibrinogen, determined by the Clauss method; VWF: Ag activity of <0.1 IU per mg fibrinogen; coagulation factor XIII activity of 0.07 IU per mg fibrinogen; 0.01-1.00 µg fibronectin per mg fibrinogen and less than 0.03 IU thrombin per mg fibrinogen.

The fibrinogen concentrate is filled into final containers after sterile filtration and the may be stored in liquid, liquid frozen or lyophilised form.

Fibrinogen produced according to this process is characterised by very low amounts of impurities which ascertain the nativity of the product and allows long term treatment of people in need. FXIII is preferable at the concentration contained, because it supports stabilisation of the formed fibrin, while an overload of this transglutaminase is avoided.

The term "comprising", "comprise" or "comprises" can also be replaced by "consisting", "consist" or "consists" without altering the disclosure of the description.

DETAILED DESCRIPTION OF THE INVENTION

Although in principle all fibrinogen containing sources can be used according to the invention, cryoprecipitate is a preferred source and in the following the cryoprecipitate serves as a typical source of fibrinogen in the further description of the manufacturing process of the invention.

Typically cryoprecipitate is reconstituted or solubilised under suitable buffer conditions in particular at about neutral pH (6.9-7.0 for example in a solution buffer containing Na-citrate and NaCl), subjected to adsorption in particular with Al(OH)$_3$ and the resulting gel removed e.g. by centrifugation. The supernatant can then become virus inactivated for example by solvent/detergent (S/D) treatment. This method is well known to the skilled person and has been originally described in EP-A-131 740. S/D compounds such as Triton (O-[4-(1,1,3,3-Tetra methylbutyl) phenoxy]-polyethoxyethanole) and TnBP (Tri-n-butylphosphate) are in particular removed by extraction with castor oil. For further purification the water-phase can be subjected to a chromatographic process. Typically this can be performed by contacting the water-phase with a strong anion-exchange gel, tri-methyl-amino-ethyl (TMAE) grafted on matrix material, such as Fractogel® EMD-TMAE. Good results are achievable if the chromatography is performed with buffers having a pH-value of 6.9-7.1 and an osmolality of 570-610 mosmol/l. Under these conditions fibrinogen is not bound to the stationary phase and hence found in the flow-through or supernatant, the latter if a batch-chromatography process is performed.

Unbound fibrinogen solution, containing typically about 40 g/l (Clauss' turbidometric method) is adjusted to pH=7.0-8.0, in particular to pH=7.3-7.5. After addition of a suitable precipitating agent, for example glycine, to a concentration of 0.8-1.2 M, in particular 0.9-1.1M the resulting solution can be stirred for 60-120 min to precipitate fibrinogen. The fibrinogen containing precipitate can then be separated by centrifugation and this intermediate fibrinogen paste might be stored at ≤−70° C., preferably at −100° C. to −70° C., for up to one month. Already a single precipitation e.g. with glycine provides a fibrinogen paste sufficiently pure for further processing.

The thus prepared intermediate can be resuspended in a 10-30 mM Tris buffer (pH=7.5 to 8.5), in particular a 15-25 mM Tris buffer with pH=7.5-8.5. The suspension obtained can then be filtered off and subjected to ultra/diafiltration for example against 5 times of the suspension volume of the same or a different buffer.

The resulting fibrinogen containing solution is then loaded onto a strong anion-exchange gel preferably selected from a group of tertiary or quaternary amino groups as ligands grafted to a matrix. Said functional groups are selected from well known diethyl-amino-ethyl (DEAE), tri-methy-amino, tri-methyl-amino-ethyl (TMAE) and other groups whereas the carrier material may be composed of cellulose, agarose, silica, polymeric or ceramic material. Good results, in particular in the reduction of fibronectin and vitronectin, can be achieved with trimethyl-amino groups grafted to a hydroxylated methacrylic polymer via a linking group such as GigaCap Q-650M®. This is very surprising as the chemically similar Marco-Prep High Q®, a methacrylic copolymer composed of diethylene-glycoldimethacrylate/glycidyl-methacrylate also with trimethyl-amino ligands but misses the hydroxyl functionality in its polymeric backbone, is less efficient in the reduction of said two proteins. The effective reduction of the sticky fibronectin is very advantageous for optional filtrations, such as ultra/diafiltration or nanofiltration, as the lifetime of filters is increased due to reduced clogging. If the process is intended to include nanofiltration, it is preferred to perform the process with a diluted solution (fibrinogen concentration of about 2 g/l), in particular with a cascade of nanofilters. The chromatographic gel or resin is in particular preequilibrated with the same buffer as used for resuspending the intermediate fibrinogen paste before applying the fibrinogen solution. Loosely bound substances were washed out with equilibration buffer followed by washing buffer (1.5 g/l sodium citrate, 6.0 g/l sodium chloride, adjusted to pH=6.8-7.2, preferably 6.9-7.1, and possessing the conductivity of 11.0-13.0 mS/cm at room temperature of 20-25° C.).

Fibrinogen can then be eluted from the chromatographic column with an elution buffer containing 1.5 g/l sodium citrate, and 10.0 g/l glycine in particular adjusted to the same pH range as the washing buffer e.g. by HCl and/or NaOH and adjusted with about 7.0 g/l NaCl to the conductivity of 13.1-15 mS/cm at room temperature of 20-25° C. Approximately 74% of the fibrinogen applied onto the column is recovered in the eluate, whilst fibronectin is almost completely removed from the fibrinogen containing eluate.

This filtered fibrinogen solution can further be concentrated by ultra/diafiltration to about 20-26 g/l and sterile filtered with membranes of ≤0.2 μm nominal pore size. Persons skilled in the art know that other concentrations, such as 1-19.9 g/l or 26.01-30 g/l or even higher are also achievable. The fibrinogen concentrate of the present invention may also be formulated with adjuvants and stabilisers known by the skilled person such as carbohydrates, e.g. sucrose, trehalose, amino acids, e.g. glycine, histidine, alanine, arginine and detergents, e.g. polyoxyethylene-(20)-sorbitan-monooleate (TWEEN 80®). This sterile filtered bulk is either optionally stored for up to 5 days at −70° C. or lower, in particular at −70° C. to −80° C., before being sterile filtered for a second time and filled into final containers and optionally freeze dried or directly filled into final containers and optionally freeze dried without a second sterile filtration.

It is not necessary to add further buffers, stabilisers, adjuvants or other compounds, like coagulation factor XIII (F XIII). Coagulation factor XIII is present in the concentrate with activities of ≥0.05 IU per mg fibrinogen (Clauss method), in particular 0.07-0.3 IU per mg fibrinogen, 0.06-0.5 IU per mg fibrinogen, or 0.05-1 IU per mg fibrinogen.

The fibrinogen concentrate produced according to the presented process reveals its nativity through a fibrinogen-antigen/fibrinogen-Clauss relation of 0.80-1.10 in particular 0.85-1.05, or 0.90-1.00; a fibrinopeptide-A content of 0.01-9.0 ng per mg fibrinogen (Clauss method), in particular 0.05-8.0 ng per mg fibrinogen or 0.08-6.0 ng per mg fibrinogen; a VWF: Ag activity of <0.1 IU per mg fibrinogen (Clauss method), in particular 0.001-0.09 IU per mg fibrinogen, 0.002-0.07 IU per mg fibrinogen, or 0.002-0.04 IU per mg fibrinogen; a factor XIII activity of ≥0.07 IU per mg fibrinogen (Clauss method), in particular 0.07-0.3 IU per mg fibrinogen, 0.08-0.5 IU per mg fibrinogen, or 0.07-1 IU per mg fibrinogen; a fibronectin content of 0.01-1.00 μg per mg fibrinogen (Clauss method), in particular 0.03-0.70 μg per mg fibrinogen or 0.05-0.40 μg per mg fibrinogen; and a plasminogen activity of 1-11 mIU per mg fibrinogen. Thrombin activity was determined to be lower than the detectable limit of 0.15 IU/ml for all runs and at the same concentrations of fibrinogen as presented in table 1, which is equivalent to less than 0.007 IU per mg fibrinogen or 0.0069-0.0001 IU/mg.

The invention is further explained by the following non-limiting example.

EXAMPLE

Cryoprecipitate, produced from plasma by established methods, was reconstituted or solubilised at about neutral pH, subjected to adsorption with $Al(OH)_3$ and the resulting gel removed by centrifugation. The supernatant was then virus inactivated by solvent/detergent (S/D) treatment. S/D compounds, Triton and TnBP were extracted with vegetable oil and the water-phase was contacted with Fractogel® EMD-TMAE. Chromatographic conditions (pH-value of 6.9-7.1 and an osmolality of 570-610 mosmol/l) were employed under which the fibrinogen did not bind to the gel and hence was found in the flow-through or supernatant.

The solution of unbound fibrinogen was stirred for about 90 minutes after addition of glycine (1 mol/l final concentration and pH=7.4) to precipitate fibrinogen. The fibrinogen containing precipitate was then separated by centrifugation, yielding an intermediate fibrinogen paste.

The thus prepared intermediate was resuspended in 20 mM Tris buffer (pH=about 8.0). The suspension obtained was then filtered and subjected to ultra/diafiltration.

The resulting fibrinogen containing solution was then loaded onto GigaCap Q650M® and the chromatographic gel or resin was preequilibrated with the same Tris buffer as used for resuspension before applying the fibrinogen solution. Loosely bound substances were washed out with the equilibration buffer followed by washing with a wash buffer (1.5 g/l sodium citrate, 6.0 g/l sodium chloride, adjusted to about pH=7.0 and a conductivity of about 12.0 mS/cm). Fibrinogen was then eluted from the chromatographic column with an elution buffer (1.5 g/l sodium citrate, and 10.0 g/l glycine adjusted to the same pH as the washing buffer and adjusted with about 7.0 g/l NaCl to the conductivity of 13.1-15 mS/cm.).

The resulting fibrinogen solution was concentrated, formulated and sterile filtered. This sterile filtered bulk was stored for 5 days at −80° C. before being sterile filtered for a second time and filled into final containers. One part of final containers was lyophilised while the other part was kept as a liquid formulation.

The products of four different production runs were analysed after reconstitution of lyophilised product. Reconstitution of lyophilisates was accomplished by addition of water for injection (WFI) up to the concentration before lyophilisation. All production runs were performed essentially in the same way as presented in the example. Results are presented in Table 1.

TABLE 1

| Run Nr. | 1 | 2 | 3 | 4 | Range |
|---|---|---|---|---|---|
| Fibrinogen Clauss (turbidimetric) [mg/ml] | 22.1 | 22.6 | 25.0 | 25.0 | 22.1-25.0 |
| Fibrinogen Antigen [mg/ml] | 20.7 | 19.1 | 22.0 | 23.0 | 19.1-23.0 |
| F XIII [IU/ml] | 2.9 | 2.5 | 2.4 | 2.6 | 2.4-2.9 |
| VWF: Ag [IU/ml] | 0.1 | 0.1 | 0.1 | 0.1 | 0.1 |
| Fibronectin [µg/ml] | 3.3 | 4.9 | 4.5 | 3.8 | 3.3-4.9 |
| Fibrinopeptide A [ng/ml] | 36 | 20 | 10 | 11 | 10-36 |

Table 2 presents the normalisation of measured values by calculation of content or activity per mg fibrinogen, determined by the Clauss method.

TABLE 2

| Run Nr. | 1 | 2 | 3 | 4 | Range |
|---|---|---|---|---|---|
| Fibrinogen Clauss [mg/ml] | 22.1 | 22.6 | 25.0 | 25.0 | 22.1-25.0 |
| mg Fibrinogen-Antigen/mg Fibr.-Clauss | 0.937 | 0.845 | 0.880 | 0.920 | 0.845-0.937 |
| IU F XIII/mg Fibr.-Clauss | 0.131 | 0.111 | 0.096 | 0.104 | 0.096-0.131 |
| IU VWF: Ag/mg Fibr.-Clauss | 0.005 | 0.004 | 0.004 | 0.004 | 0.004-0.005 |
| µg Fibronectin/mg Fibr.-Clauss | 0.149 | 0.217 | 0.180 | 0.152 | 0.149-0.217 |
| ng Fibrinopeptide A/mg Fibr.-Clauss | 1.629 | 0.885 | 0.400 | 0.440 | 0.400-1.629 |

Comparison with commercially available products.

Table 3 depicts measured values of commercially available fibrinogen concentrates. All products were lyophilized products and were reconstituted according to manufacturers' guidelines. Also shown is the range of values of runs 1-4 according to the present invention as already shown in table 1.

TABLE 3

|  | product 1 | product 2 | product 3 | present invention |
|---|---|---|---|---|
| Fibrinogen Clauss (turbidimetric) [mg/ml] | 11.5 | 9.8 | 23.7 | 22.1-25.0 |
| Fibrinogen Antigen [mg/ml] | 16.3 | 19.1 | 21.0 | 19.1-23.0 |
| F XIII [IU/ml] | <0.2 | <0.2 | 1 | 2.4-2.9 |
| VWF: Ag [IU/ml] | 14 | 1.3 | 3.8 | 0.1 |
| Fibronectin [µg/ml] | 13.3 | 258.9 | 944.3 | 3.3-4.9 |
| Fibrinopeptide A [ng/ml] | 130 | 1843 | 814 | 10-36 |

Table 4 presents the normalisation of measured values of commercially available products by calculation of content or activity per mg fibrinogen, determined by the Clauss method. Also shown is the range of values of runs 1-4 according to the present invention as already shown in table 2.

TABLE 4

|  | product 1 | product 2 | product 3 | present invention |
|---|---|---|---|---|
| Fibrinogen Clauss (turbidimetric) [mg/ml] | 11.5 | 9.8 | 23.7 | 22.1-25.0 |
| mg Fibrinogen-Antigen/mg Fibr.-Clauss | 1.417 | 1.949 | 0.886 | 0.845-0.937 |
| IU F XIII/mg Fibr.-Clauss | <0.017 | <0.020 | 0.042 | 0.096-0.131 |
| IU VWF: Ag/mg Fibr.-Clauss | 1.217 | 0.133 | 0.160 | 0.004-0.005 |
| µg Fibronectin/mg Fibr.-Clauss | 1.157 | 26.418 | 39.844 | 0.149-0.217 |
| ng Fibrinopeptide A/mg Fibr.-Clauss | 11.304 | 188.061 | 34.346 | 0.400-1.629 |

Comparison with a preferred embodiment of WO 01/48016.

1 g Fraction I paste was extracted with 8.33 g extraction buffer (0.8M NaCl, 5 mM ε-ACA (epsilon-aminocaproic acid), 20 mM Na-citrate, 60 IU/ml heparin and pH=7.3, i.e. the improved buffer of paragraph 1.1.19) at 37° C. for 2 hours. 50 g of a 2% aluminium hydroxide (alhydrogel) solution were added to the supernatant of the extraction. The mixture was stirred 15 minutes at room temperature, centrifuged at 5000 g for 10 minutes and the pellet was discarded. The alhydrogel supernatant and a Glycin/NaCl buffer (2.1M glycine, 20 mM Na-citrate, 3.6M NaCl and 2.4 mM $CaCl_2$) were brought to 30.2° C. respectively 29.7° C. and the supernatant was added to the buffer within 4.5 minutes. The mixture of 1 part supernatant and 2.05 parts buffer was stirred for 20 minutes at 30.2-31.1° C. and afterwards centrifuged for 10 minutes at 5000 g. The Gly/NaCl-precipitate was resolubilised in buffer D representing ⅓ of the volume of the supernatant of the fraction 1 paste extraction at about 21° C. at continuous stirring for 2 hours. The resolubilised precipitate was thereafter S/D treated with Polysorbate 80 and TnBP for 1 hour at concentrations of 1% (Polysorbate 80) and 0.3% (TnBP) at about 23° C. Anion exchange chromatography was performed with Macro-Prep® HQ resin in an XK26 column and about 20 cm bed height representing about 100 ml column volume at a flow rate of 10 ml/min. equilibration took place with 2 column volumes of improved MQ buffer (50 mM TRIS, 100 mM NaCl, 20 mM ε-ACA at pH=8.0, paragraph 2.2.3) and conductivity (post column) reaching the given boundaries of conductivity+−10% of MQ buffer. After washing with 6 column volumes of MQ buffer, fibrinogen was eluted in a single peak with improved buffer ME (500 mM NaCl, 1.1 mM $CaCl_2$, 10 mM Na-citrate, 10 mM Tris and 45 mM sucrose at pH=7.0, i.e. buffer D+2×200 mM NaCl). Analytical results are presented in table 5.

TABLE 5

|  | WO 01/48016 | present invention |
|---|---|---|
| Fibrinogen Clauss (turbidimetric) [mg/ml] | 5.90 | 22.1-25.0 |
| mg Fibrinogen-Antigen/mg Fibr.-Clauss | 0.845 | 0.845-0.937 |
| IU F XIII/mg Fibr.-Clauss | 0.440 | 0.096-0.131 |

TABLE 5-continued

|  | WO 01/48016 | present invention |
|---|---|---|
| IU VWF: Ag/mg Fibr.-Clauss | 0.100 | 0.004-0.005 |
| µg Fibronectin/mg Fibr.-Clauss | 10.83 | 0.149-0.217 |
| ng Fibrinopeptide A/mg Fibr.-Clauss | 6.02 | 0.400-1.629 |

The invention claimed is:

1. A fibrinogen product having fibronectin content of 0.01-1.00 µg per mg Fibrinogen-Clauss obtainable by a process comprising the following steps:
   a) solubilisation of cryoprecipitate, solubilised at about neutral pH;
   b) subjecting the solution to adsorption with Al(OH)$_3$ and removing a resulting gel;
   c) virus inactivating the resulting solution of step b) by a solvent/detergent (S/D) treatment with Triton and TnBP, extraction of S/D reagents with vegetable oil and contacting the water-phase with a TMAE resin at a pH-value of 6.9-7.1 and an osmolality of 570-610 mosmol/l;
   d) precipitation of Fibrinogen-Clauss, which is found in the flow-through or supernatant of step c), by 1M glycine, and separation of a Fibrinogen-Clauss paste;
   e) resuspension of the Fibrinogen-Clauss paste in a 20 mM TRIS buffer at a pH of about 8.0, and filtration;
   f) loading the filtered solution of step e) onto a strong anion exchange resin comprising trimethyl-amino groups grafted to a hydroxylated methacrylic polymer backbone via linking groups and washing off loosely bound substances with a wash buffer of about 12.0 mS/cm conductivity;
   g) elution of Fibrinogen-Clauss with an elution buffer containing about 1.5 g/l sodium citrate, about 7.0 g/l sodium chloride and about 10.0 g/l glycine, adjusted to a pH of about 7.0 and a conductivity of 13.1-15 mS/cm; and
   h) concentrating, formulating, sterile filtering and filling into containers.

2. A fibrinogen product having the following properties:
   20-26.0 mg/ml Fibrinogen-Clauss (turbidimetric);
   0.8-1.1 mg Fibrinogen-Antigen/mg Fibrinogen-Clauss;
   0.07-1.0 IU F XIII/mg Fibrinogen-Clauss;
   0.01-1.0 µg Fibronectin/mg Fibrinogen-Clauss; and
   0.01-9.0 ng Fibrinopeptide A/mg Fibrinogen-Clauss.

3. The fibrinogen product of claim 2, obtainable by a process comprising the following steps:
   a) solubilisation of cryoprecipitate, solubilised at about neutral pH;
   b) subjecting the solution to adsorption with Al(OH)$_3$ and removing a resulting gel;
   c) virus inactivating the resulting solution of step b) by S/D treatment with Triton and TnBP, extraction of S/D reagents with vegetable oil and contacting the water-phase with a TMAE resin at a pH-value of 6.9-7.1 and an osmolality of 570-610 mosmol/l;
   d) precipitation of Fibrinogen-Clauss, which is found in the flow-through or supernatant of step c), by 1M glycine, and separation of a Fibrinogen-Clauss paste;
   e) resuspension of the Fibrinogen-Clauss paste in a 20 mM TRIS buffer at a pH of about 8.0, and filtration;
   f) loading the filtered solution of step e) onto a strong anion exchange resin comprising trimethyl-amino groups grafted to a hydroxylated methacrylic polymer backbone via linking groups and washing off loosely bound substances with a wash buffer of about 12.0 mS/cm conductivity;
   g) elution of Fibrinogen-Clauss with an elution buffer containing about 1.5 g/l sodium citrate, about 7.0 g/l sodium chloride and about 10.0 g/l glycine, adjusted to a pH of about 7.0 and a conductivity of 13.1-15 mS/cm; and
   h) concentrating, formulating, sterile filtering and filling into containers.

4. The fibrinogen product according to claim 3, having a fibronectin content of 0.1-1.00 µg per mg Fibrinogen-Clauss.

5. The fibrinogen product according to claim 3, characterized in that it is in lyophilized state.

6. A fibrinogen product having the following properties:
   a fibrinogen-antigen/fibrinogen relation of 0.80 to 1.10;
   a fibrinopeptide-A content of 0.01 to 9.0 ng per mg fibrinogen,
   a VWF:Ag activity of <0.1 IU per mg fibrinogen;
   a factor XIII activity of >0.07 IU per mg fibrinogen;
   a fibronectin content of 0.01-1.00 µg per mg fibrinogen; and
   a plasminogen concentration of 1 to 11 mIU,
wherein the fibrinogen content is determined by the turbidimetric Clauss method.

7. The fibrinogen product according to claim 6, wherein the fibrinopeptide-A content is 0.05 to 8.0 ng per mg fibrinogen; and
   the factor XIII activity is 0.07 to 0.3 IU per mg fibrinogen.

8. The fibrinogen product according to claim 7, wherein the fibrinogen-antigen/fibrinogen relation is 0.85 to 1.05;
   the VWF:Ag activity is 0.001 to 0.09 IU per mg fibrinogen; and
   the fibronectin content is 0.03-0.70 µg per mg fibrinogen.

9. The fibrinogen product according to claim 6, wherein the fibrinogen-antigen/fibrinogen relation is 0.90 to 1.00;
   the fibrinopeptide-A content is 0.08 to 6.0 ng per mg fibrinogen,
   the VWF:Ag activity is 0.002 to 0.07 IU per mg fibrinogen;
   the factor XIII activity is 0.08 to 0.5 IU per mg fibrinogen; and
   the fibronectin content is 0.05 to 0.40 µg per mg fibrinogen.

10. The fibrinogen product according to claim 6 obtainable by a process comprising the following steps:
    a) solubilisation of cryoprecipitate, solubilised at about neutral pH;
    b) subjecting the solution to adsorption with Al(OH)$_3$ and removing a resulting gel;
    c) virus inactivating the resulting solution of step b) by S/D treatment with Triton and TnBP, extraction of S/D reagents with vegetable oil and contacting the water-phase with a TMAE resin at a pH-value of 6.9-7.1 and an osmolality of 570-610 mosmol/l;
    d) precipitation of fibrinogen, which is found in the flow-through or supernatant of step c), by 1M glycine, and separation of a fibrinogen paste;
    e) resuspension of the fibrinogen paste in a 20 mM TRIS buffer at a pH of about 8.0, and filtration;
    f) loading the filtered solution of step e) onto a strong anion exchange resin comprising trimethyl-amino groups grafted to a hydroxylated methacrylic polymer backbone via linking groups and washing off loosely bound substances with a wash buffer of about 12.0 mS/cm conductivity;

g) elution of fibrinogen with an elution buffer containing about 1.5 g/l sodium citrate, about 7.0 g/l sodium chloride and about 10.0 g/l glycine, adjusted to a pH of about 7.0 and a conductivity of 13.1-15 mS/cm; and h) concentrating, formulating, sterile filtering and filling into containers.

11. The fibrinogen product according to claim 10, characterized in that it is in lyophilized state.

* * * * *

UNITED STATES PATENT AND TRADEMARK OFFICE
CERTIFICATE OF CORRECTION

| | | |
|---|---|---|
| PATENT NO. | : 9,938,318 B2 | Page 1 of 1 |
| APPLICATION NO. | : 15/164736 | |
| DATED | : April 10, 2018 | |
| INVENTOR(S) | : Petra Schulz et al. | |

It is certified that error appears in the above-identified patent and that said Letters Patent is hereby corrected as shown below:

In the Claims

Column 9, Claim 1, Line 25, "precipitation of Fibrinogen-Clauss," should be -- precipitation of fibrinogen, --

Column 9, Claim 1, Line 27, "and separation of a Fibrinogen-Clauss paste;" should be -- and separation of a fibrinogen paste; --

Column 9, Claim 1, Line 28, "resuspension of the Fibrinogen-Clauss paste" should be -- resuspension of the fibrinogen paste --

Column 9, Claim 1, Line 36, "elution of Fibrinogen-Clauss with an elution buffer" should be -- elution of fibrinogen with an elution buffer --

Column 9, Claim 3, Line 60, "precipitation of Fibrinogen-Clauss," should be -- precipitation of fibrinogen, --

Column 9, Claim 3, Line 62, "and separation of a Fibrinogen-Clauss paste;" should be -- and separation of a fibrinogen paste; --

Column 9, Claim 3, Line 63, "resuspension of the Fibrinogen-Clauss paste" should be -- resuspension of the fibrinogen paste --

Column 10, Claim 3, Line 4, "elution of Fibrinogen-Clauss with an elution buffer" should be -- elution of fibrinogen with an elution buffer --

Signed and Sealed this
Eighth Day of January, 2019

Andrei Iancu
*Director of the United States Patent and Trademark Office*